United States Patent
Kocinska et al.

(10) Patent No.: US 11,331,252 B2
(45) Date of Patent: *May 17, 2022

(54) DENTIFRICE INCLUDING ZINC AND BLUE DYE OR PIGMENT

(71) Applicant: Colgate-Palmolive Company, New York, NY (US)

(72) Inventors: Agnieszka Kocinska, Basel (CH); Suman Chopra, Monroe, NJ (US); Jennifer Gronlund, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/324,789

(22) PCT Filed: Aug. 11, 2016

(86) PCT No.: PCT/US2016/046538
§ 371 (c)(1),
(2) Date: Feb. 11, 2019

(87) PCT Pub. No.: WO2018/031017
PCT Pub. Date: Feb. 15, 2018

(65) Prior Publication Data
US 2019/0183757 A1    Jun. 20, 2019

(51) Int. Cl.
*A61K 8/27*    (2006.01)
*A61Q 11/00*   (2006.01)
*A61K 8/49*    (2006.01)
*A61K 8/365*   (2006.01)

(52) U.S. Cl.
CPC ............... *A61K 8/27* (2013.01); *A61K 8/365* (2013.01); *A61K 8/494* (2013.01); *A61K 8/4913* (2013.01); *A61Q 11/00* (2013.01); *A61K 2800/28* (2013.01); *A61K 2800/30* (2013.01); *A61K 2800/43* (2013.01)

(58) Field of Classification Search
CPC ........ A61K 8/27; A61K 8/494; A61K 8/4913; A61K 8/365; A61K 2800/30; A61K 2800/28; A61K 2800/43; A61Q 11/00
See application file for complete search history.

(56) References Cited

U.S. PATENT DOCUMENTS

| | | | |
|---|---|---|---|
| 3,929,987 A | 12/1975 | Colodney et al. | |
| 6,416,744 B1 | 7/2002 | Robinson | |
| 9,901,521 B2 | 2/2018 | Maloney | |
| 9,931,292 B2 | 4/2018 | Boyd et al. | |
| 2005/0038181 A1 | 2/2005 | Chopra et al. | |
| 2007/0122361 A1 | 5/2007 | Weitao | |
| 2013/0078198 A1* | 3/2013 | Aitken | A61K 8/347 424/56 |
| 2013/0236400 A1* | 9/2013 | Lewus | A61K 8/03 424/52 |
| 2016/0331653 A1 | 11/2016 | Maloney | |
| 2016/0331663 A1* | 11/2016 | Maloney | A61K 8/463 |
| 2019/0021963 A1 | 1/2019 | Maloney | |

FOREIGN PATENT DOCUMENTS

| | | | |
|---|---|---|---|
| CA | 2927282 | 6/2015 | |
| CN | 101227883 | 7/2008 | |
| CN | 105813620 | 7/2016 | |
| EP | 1935395 | 6/2008 | |
| RU | 2297772 | 4/2007 | |
| WO | 1994/026245 | 11/1994 | |
| WO | 2007013937 | 2/2007 | |
| WO | WO-2015095709 A1 * | 6/2015 | A61K 8/19 |
| WO | 2015/099642 | 7/2015 | |

OTHER PUBLICATIONS

International Search Report and Written Opinion of the International Searching Authority in international Application No. PCT/US2016/046538, dated Dec. 13, 2016.
Procter & Gamble, 2015, "Whitening Fluoride Toothpaste," Database Mintel GNPD AN: 3014533.
Procter & Gamble, 2016, "Daily 2-Step System," Database Mintel GNPD AN: 3863185.
Procter & Gamble, 2016, "Healthy Freshness Fluoride," Database Mintel GNPD AN: 3950141.

* cited by examiner

Primary Examiner — Snigdha Maewall

(57) ABSTRACT

A whitening dentifrice composition includes a blue coloring agent, a zinc salt, and an orally acceptable vehicle. The blue coloring agent is selected from the group consisting of a blue pigment and a blue dye. The blue pigment has a blue to blue-violet color with a hue angle in the CIELAB system ranging from 200 degrees to 320 degrees. The whitening dentifrice composition provides a greater whitening benefit to a tooth surface in comparison to a dentifrice composition that does not contain the zinc salt.

10 Claims, No Drawings

DENTIFRICE INCLUDING ZINC AND BLUE DYE OR PIGMENT

BACKGROUND

Whitening agents, such as blue dye or blue pigment, are added to oral care compositions to make teeth appear whiter. For example, the blue dye or blue pigment may be present in a toothpaste, and a user may apply the toothpaste while brushing. The blue dye or blue pigment may be deposited on the surface of the teeth (e.g., while brushing), and the blue dye or blue pigment may make yellow stains on the teeth appear whiter.

The blue dye or blue pigment may only remain on the surface of the teeth for a limited duration, allowing the yellow stains to eventually reappear. In addition, high concentrations of blue dye or blue pigment may stain the soft tissues in the mouth or leave the teeth looking "too blue" for some consumers. Thus, while such conventional, whitening oral care compositions are useful for whitening teeth, new and improved formulations are desired.

BRIEF SUMMARY

A whitening dentifrice composition is disclosed. The composition includes a blue coloring agent, a zinc salt, and an orally acceptable vehicle. The blue coloring agent is selected from the group consisting of a blue pigment and a blue dye. The blue pigment has a blue to blue-violet color with a hue angle in the CIELAB system ranging from 200 degrees to 320 degrees. The whitening dentifrice composition provides a greater whitening benefit to a tooth surface in comparison to a dentifrice composition that does not contain the zinc salt.

In another embodiment, the whitening dentifrice composition includes a blue dye, a zinc salt, water, and an orally acceptable vehicle. The zinc salt is present in an amount from about 0.1 wt % to about 5 wt %. The water is present in an amount from about 25% to about 80%. The whitening dentifrice composition including the zinc salt provides a greater initial whitening benefit and a longer-lasting whitening benefit to a tooth surface than a dentifrice composition including the same amount of water and no zinc salt.

A method for whitening a tooth surface in a human or animal is also disclosed. The method includes applying a whitening dentifrice composition to the tooth surface. The whitening dentifrice composition includes a blue coloring agent, zinc lactate, and an orally acceptable vehicle. The blue coloring agent is selected from the group consisting of a blue pigment and a blue dye. The blue pigment has a blue to blue-violet color with a hue angle in the CIELAB system ranging from 200 degrees to 320 degrees. The zinc lactate is present in an amount from about 0.1 wt % to about 5 wt %. The whitening dentifrice composition provides a greater whitening benefit to the tooth surface than a dentifrice composition including other zinc salts or no zinc salt.

Further areas of applicability of the present disclosure will become apparent from the detailed description provided hereinafter. It should be understood that the detailed description and specific examples, while indicating typical embodiments, are intended for purposes of illustration only and are not intended to limit the scope of the disclosure.

DETAILED DESCRIPTION

The following description of the embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Compositions

The present inventors have surprisingly discovered that zinc may be included in a whitening dentifrice composition, which also includes a blue dye and/or a blue pigment, to further enhance whitening efficacy. Without being bound by theory, it is believed that zinc improves an instant whitening effect of a dentifrice composition that includes a blue dye or blue pigment. More particularly, the zinc may facilitate the (e.g., initial) deposition of the blue dye or blue pigment on the surface of the teeth. The zinc may also cause the blue dye or blue pigment to remain on the surface of the teeth for a greater duration. As discussed in more detail below, the blue dye may be blue dye No. 1, and the blue pigment may be blue pigment 15.

It is also believed that the present oral care dentifrices may be formulated with reduced amounts of blue dye or blue pigment without a concomitant decrease in whitening efficacy. Additionally, the addition of zinc to a dentifrice composition may increase the level (e.g., percentage) of water that may be used in the dentifrice composition without a negative impact on the whitening efficacy. Accordingly, the present stable whitening oral care dentifrice compositions exhibit improved properties in comparison to art-known whitening compositions.

Zinc

In some embodiments, zinc may be included in the dentifrice compositions of the present disclosure. The zinc (e.g., the zinc ions) may be present in the composition in an amount ranging from about 0.01% to about 1% by weight, about 0.1% to about 0.9% by weight, about 0.2% to about 0.8% by weight, about 0.3% to about 0.7% by weight. In some embodiments, the zinc may be or include a zinc salt such as zinc lactate, zinc oxide, zinc chloride, zinc phosphate, or zinc citrate. The zinc salt may be present in the composition in an amount ranging from about 0.01% to about 5%, about 0.1% to about 4%, about 0.2% to about 3%, about 0.3% to about 2%, or about 0.5% to about 2.5% by weight. For example, the composition may include about 2% zinc lactate by weight.

Core Shell Silica

In at least one embodiment, the dentifrice composition may include less than or equal to about 1%, about 0.5%, or about 0.1% shell silica (e.g., core shell silica) by weight. For example, the dentifrice composition may include 0% core shell silica by weight. As mentioned above, the zinc in the dentifrice composition may facilitate the (e.g., initial) deposition of the blue dye or blue pigment on the surface of the teeth and/or cause the blue dye or blue pigment to remain on the surface of the teeth for a greater duration. This may allow core shell silica to be omitted from the dentifrice composition because the core shell silica is not needed to facilitate the (e.g., initial) deposition of the blue dye or blue pigment on the surface of the teeth and/or cause the blue dye or blue pigment to remain on the surface of the teeth for a greater duration.

Coloring Agent

As used herein, the term "coloring agent" refers to a substance in the form of a dry powder or liquid that imparts color to another substance. Generally, coloring agents include pigments, dyes, lakes, or combinations thereof.

Pigments

In some embodiments, the dentifrice compositions of the present disclosure may include a pigment. As used herein, a "pigment" is a synthetic or natural water insoluble substance, which imparts color to another substance. In some embodiments, the pigments further enhance the whiteness of the teeth. As is known in the art, the visual perception of a white substance can be altered through the deposition of an optical brightener, a blue pigment, or a blue dye. This effect is commonly used in laundry detergent products to make white clothes appear "whiter" to the human eye. The same concept has been applied to tooth whitening. See PCT Publication No. WO 2015/099642 to Colgate-Palmolive Company, which is herein incorporated by reference in its entirety.

In some embodiments, the pigment included in the present stable whitening oral care dentifrice compositions may have a hue angle, h, in the CIELAB system ranging from about 200 degrees to about 320 degrees, typically between about 250 degrees and about 290 degrees. As is well known in the art, "CIELAB" is a color measurement system adopted by the Commission Internationale de l'Eclairage (CIE) in 1976. It is based on a three-dimensional color space. The system was developed to represent color in a manner that is consistent with human vision and proportional to perceived color differences. CIELAB values describe the coordinates of a specific color in a three dimensional space. There are three axes: L* describing light to dark, b* for blue to yellow, and a* for red to green. Any point in the three dimensional CIELAB color space can be described by its L* a* and b* coordinates. The same point can also be described by L*, hue angle and chroma, which uses cylindrical coordinates. The Hue angle is defined by the formula: $H_{ab}=\tan-1(b^*/a^*)$, wherein a* and b* are coordinates in the L*a*b* color space. A detailed description of hue angle may be found in M L Gulrajani (Ed.). (2010). *Colour Measurement: Principles, Advances and Industrial Applications*. Cambridge, United Kingdom: Woodhouse Publishing, which is herein incorporated by reference in its entirety.

The pigment used in the dentifrice compositions is capable of reflecting sufficient light such that the treated tooth is perceivably whiter than its initial color. In some embodiments, the pigment may be colored such that its natural color is within the violet-red to green-blue color. More particularly, the pigment may be violet or blue, e.g., one of those listed in the Colour Index International. These pigments are listed as pigment violet 1 through to pigment violet 56 and pigment blue 1 through 83. In some embodiments, the pigment violets may be pigment violet 1, 1:1, 1:2, 2, 3, 5:1, 13, 19, 23, 25, 27, 31, 32, 37, 39, 42, 44 and 50. In some embodiments, the pigment blues may be pigment blue 1, 2, 9, 10, 14, 15, 15:1, 15:2, 15:3, 15:4, 15:6 16, 18, 19, 24:1, 25, 56, 60, 61, 62 and 66. Other suitable pigments are pigment ultramarine blue and ultramarine violet. Typically, the pigment is Pigment Blue 15, more typically Pigment Blue 15:1, 15:2, 15:3, 15:4, 15:5 or 15:6, most typically 15:1.

While blue or violet single pigments may be used in the dentifrice compositions, the same effect may be achieved through mixing pigments outside of the hue angle range of about 200 degrees to about 320 degrees. The desired hue angle may instead be obtained by mixing a red and green-blue pigment to yield a blue or violet shaded pigment.

The amount of pigment in the composition may be from about 0.01% to about 0.3%, about 0.01% to about 0.15%, or about 0.01% to 0.08% by weight, such as about 0.05%. In other embodiments, the amount of pigment in the composition may be from about 0.01% to about 0.05%, about 0.05% to about 0.1%, or about 0.1% to 0.15% by weight. The pigment may be uniformly spread throughout the composition or may be dispersed in a second phase such as a stripe or other coextruded second phase. Such "dual phase" compositions have the advantage that the phases may be differently colored, presenting a more visually attractive product to the consumer.

Dyes

As used herein, the term "dye" refers to an organic species, which is essentially water soluble in an aqueous medium in which the dye remains chemically stable. The dyes used with the dentifrice composition of the present disclosure are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-m ethylene}-[1-N-ethyl-N-p-sulfobenzyl)-.DELTA.-3,5-cyclohexadienimine], FD&C Blue No. 1 (disodium salt of dibenzyldiethyl-diaminotriphenylcarbinol trisulfonic acid anhydride), FD&C Blue No. 2 (sodium salt of disulfonic acid of indigotin) D&C Green No. 5, D&C Orange No. 5, D&C Red No. 21, D&C Red No. 22, D&C Red No. 27, D&C Red No. 28, D&C Red No. 30, D&C Red No. 40, D&C Yellow No. 10 and mixtures thereof in various proportions.

The amount of dye in the dentifrice composition may be from about 0.01% to about 0.3%, about 0.01% to about 0.15%, or about 0.01% to 0.08% by weight, such as about 0.05%. In other embodiments, the amount of dye in the composition may be from about 0.01% to about 0.05%, about 0.05% to about 0.1%, or about 0.1% to 0.15% by weight. The dye may be uniformly spread throughout the composition or may be dispersed in a second phase such as a stripe or other coextruded second phase. Such "dual phase" compositions have the advantage that the phases may be differently colored, presenting a more visually attractive product to the consumer.

Lakes

As used herein, "lakes" are manufactured by attaching dye molecules to insoluble reactive or adsorptive substratum, such as aluminum hydroxide particles, thereby rendering them water-insoluble. Lakes which may be used with the stable whitening dentifrice composition of the present disclosure include but are not limited to FD&C Blue No. 1 Lake, FD&C Blue No. 2 Lake, FD&C Green No. 3 Lake, FD&C Red No. 3 Lake, FD&C Red No. 40 Lake, FD&C Yellow No. 5 Lake, FD& C Yellow No. 6 Lake. In certain embodiments the colorant is selected from FD&C Blue No. 1 Lake, FD&C Yellow No. 5 Lake, and FD&C Red No. 40 Lake.

Water

The dentifrice composition may be or include a "low-water" dentifrice composition or a "high-water" dentifrice composition. The amount of water in a low-water dentifrice composition may be from about 0% to about 25% by weight.

For example, the amount of water in a low-water dentifrice composition may be from about 0% to about 5%, about 5% to about 10%, about 10% to about 15%, about 15% to about 20%, or about 20% to about 25% by weight. The amount of water in a high-water dentifrice composition may be from about 25% to about 80% by weight. For example, the amount of water in a high-water dentifrice composition may be from about 25% to about 35%, about 35% to about 45%, about 45% to about 55%, about 55% to about 65%, or about 65% to about 80% by weight. The addition of zinc to the dentifrice composition may allow the dentifrice composition to include more water (e.g., be a high-water dentifrice composition) without a negative impact on the whitening efficacy.

Whitening Agents

As used herein a "whitening agent" is a material which effects whitening of a tooth surface to which it is applied. Any whitening agent known or developed in the art may be used in the present stable whitening oral care dentifrice compositions. For example, in some embodiments, the whitening agent is an oxidizing agent, a reducing agent, or combinations thereof. In its broadest sense, "oxidizing agent" is intended to include those compounds which can accept an electron from another molecule in the environment of the oral cavity without having a deleterious or unacceptably harmful affect on the oral cavity in normal and accepted use.

Oxidizing agents suitable for use with the present dentifrice compositions include peroxides, chlorites, and hypochlorites. Examples of suitable chlorites and hypochlorites include those having alkali or alkaline metal cations and include calcium chlorite, barium chlorite, magnesium chlorite, lithium chlorite, sodium chlorite, potassium chlorite, calcium hypochlorite, barium hypochlorite, magnesium hypochlorite, lithium hypochlorite, lithium hypochlorite, and sodium hypochlorite.

In various embodiments, the whitening agent may include a peroxide compound. As referred to herein, a "peroxide compound" is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. The peroxide compound may include hydrogen peroxide, urea peroxide, sodium percarbonate or mixtures thereof. In some embodiments, the present dentifrice compositions may not include a peroxide (i.e., be peroxide-free). For example, the present dentifrice compositions may not include a peroxide when the coloring agent is a blue pigment.

In other embodiments, the whitening agent is a reducing agent. In its broadest sense, this term is intended to include those compounds which can donate an electron to another molecule in the environment of the oral cavity without having a deleterious or unacceptably harmful affect on the oral cavity in normal and accepted use. Synonyms for this term are preservatives or anti-oxidizing agents. There are numerous compounds which have been proven to be useful as reducing agents. A list of such compounds currently recognized for this purpose can be found in reference manuals and compendia covering pharmaceutical and oral care products. Suitable examples include vitamin C and its esters, vitamin E, the benzoates and hydroxybenzoates, butylated hydroxytoluene (BHT), butylated hydroxyanisole (BHA) and other reducing phenols, derivatives of dihydroxyquinoline, derivatives of polymerized 2,2,4-trimethyl-1,2-dihydroquinoline and alkyl gallate such as dodecyl gallate, ethyl gallate, octyl gallate and propyl gallate. In some embodiments, vitamin C, vitamin E, BHA, BHT, propyl gallate and combinations thereof are used.

In various embodiments, the whitening agent may include from about 4.1% to about 50% w/w, such as about 4.1% to about 40% w/w, or such as about 4.1% to about 30% w/w of the present dentifrice compositions. In other embodiments, the whitening agent, such as a peroxide, may be present in a low concentration (e.g., from about 0.01% to about 4%, about 0.01% to about 3%, about 0.05% to about 3%, about 0.075% to about 2%, about 0.1% to about 1.5%, about 0.01% to about 0.3%, or about 0.1% to about 0.3% or about 0.1%).

Complexed Whitening Agents

In some embodiments, the present dentifrice compositions include a whitening complex. As used herein a "whitening complex" includes a whitening agent as described herein complexed with a polymer or copolymer, which releases the whitening agent upon exposure to highly aqueous environments, such as in the oral cavity. As used herein, a "complex" is an entity formed by a loose association involving two or more molecular entities (ionic or uncharged), e.g., a whitening agent and a polymer.

The term "polymer" as used herein, is given its ordinary meaning as used in the art, i.e., a molecular structure including one or more repeat units (monomers), connected by covalent bonds. The repeat units may all be identical, or in some cases, there may be more than one type of repeat unit present within the polymer. If more than one type of repeat unit is present within the polymer, then the polymer is said to be a "copolymer." It is to be understood that in any embodiment employing a polymer, the polymer being employed may be a copolymer. The repeat units forming the copolymer may be arranged in any fashion. For example, the repeat units may be arranged in a random order, in an alternating order, or as a block copolymer, i.e., including one or more regions that each include a first repeat unit (e.g., a first block), and one or more regions that each include a second repeat unit (e.g., a second block), etc. Block copolymers may have two (a diblock copolymer), three (a triblock copolymer), or more numbers of distinct blocks.

The whitening agent associated with a polymer of the present application may include polymers that are cross-linked and are capable of absorbing, adsorbing, complexing or otherwise associating with the provided whitening agent of the present application. Further, the polymer is suitably facilitated to retain the whitening agent of the present application. Such retained whitening agent source discharges the whitening agent when it is applied onto the teeth for whitening.

Suitable polymers and co-polymers include N-vinyl lactam based polymers and copolymers. The monomers for preparing a vinyl lactam-based polymer or co-polymer of the present application includes any monomer having 3 to 8 atoms in a heterocyclic ring, comprising a carbonyl carbon atom and a heteroatom (such as N, S, O) in its vinyl moiety.

Suitable monomers include but not limited to N-vinyl-2-pyrrolidone, N-vinyl-2-piperidone, N-vinyl-3-methyl-pyrrolidinone, N-vinyl-3-methyl-piperidone, N-vinyl-3-methyl-caprolactam, N-vinyl-4-methyl-pyrrolidinone, N-vinyl-4-methyl-2-pyrrolidone, N-vinyl-4-methyl-piperidone, N-vinyl-4-methyl-caprolactam, N-vinyl-5-methyl-pyrrolidinone, N-vinyl-5-ethyl-2-pyrrolidone, N-vinyl-4-methyl-piperidone, N-vinyl-3-ethyl-pyrrolidinone, N-vinyl-4,5-dimethyl-pyrrolidinone, N-vinyl-5,5-dimethyl-pyrrolidinone, N-vinyl-3,3,5-trimethyl-pyrrolidinone, N-vinyl-5-methyl-5-ethyl-pyrrolidinone, N-vinyl-3,4,5-trimethyl-3-ethyl-pyrrolidinone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-2-caprolactam, N-vinyl-7-methyl-caprolactam, N-vinyl-7-ethyl-caprolactam, N-vinyl-3,5-dimethyl-caprolactam, N-vinyl-4,6-dimethyl-caprolactam, N-vinyl-3,5,7-trimethyl-caprolactam, N-vinyl-2-valerolactam, N-vinyl-hexahydro-2-azepinone, N-vinyl-octahydro-2-azocinone, N-vinyl octahydro-2-azoninone, and N-vinyl decahydro-2-azecinone.

The polymer may be a cross-linked polyvinylpyrrolidone, also known as poly-N-vinyl-poly-2-pyrrolidone, and commonly abbreviated to cross-linked "PVP." PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit may include a polar imide group, four non-polar methylene groups, and a non-polar methane group. Cross linked PVP includes those commercially available as Kollidon® and Luvicross®, marketed by BASF, Mount Olive, N.J., USA; and PolyPlasdone® INF-10, marketed by ISP Corporation, Wayne, N.J., USA.

In some embodiments, the cross-linked polyvinylpyrrolidone is complexed with a peroxide whitening agent, such as hydrogen peroxide (hereinafter "PVP—$H_2O_2$"). Upon exposure to highly aqueous environments, such as in the oral cavity, the PVP—$H_2O_2$ dissociates into individual species (PVP polymer and $H_2O_2$). Suitable cross-linked complexes of PVP—$H_2O_2$ are known in the art and are disclosed, for example, in U.S. Pat. No. 5,122,370, which is herein incorporated by reference in its entirety. Commercially available complexes of hydrogen peroxide adsorbed to cross-linked polyvinylpyrrolidone include, for example, Peroxydone XL-10 and Peroxydone K-30, marketed by ISP Corporation, Wayne, N.J., USA.

Some embodiments of the present disclosure provide dentifrice compositions including from about 0.05% to about 25%, about 0.1% to about 15%, about 0.25% to about 10%, about 0.5% to about 10%, or about 0.5% to about 8%, by weight cross-linked polyvinylpyrrolidone complexed with a whitening agent. In other embodiments, the dentifrice compositions include about 0.5% to about 5%, about 0.5% to about 3%, about 0.5% to about 2%, or about 0.05% to about 0.55% by weight cross-linked polyvinylpyrrolidone complexed with a whitening agent, such as about 0.055%. In some embodiments, the whitening complex may contain about 1.0-30 wt %, (for example, 15-25 wt %, or for example about 17-22 wt %) of hydrogen peroxide and about 5-15 wt %, for example about 7-12 wt %, of total nitrogen, for example, having substantially the same specifications as Peroxydone XL-10, e.g., available from International Specialty Products (Wayne, NX).

In some embodiments, the dentifrice compositions further include from about 1% to about 20%, such as about 1% to about 15%, such as about 1% to about 10%, such as about 5% to about 15%, such as about 6% to about 12%, such as about 8% to about 11%, such as about 8.5% to about 11%, such as about 9.9% to about 10%, or such as about 5.75% by weight of a cross-linked polymer, such as cross-linked polyvinylpyrrolidone, which is in addition to the cross-linked polymer or co-polymer included in the whitening complex.

In other embodiments, the dentifrice compositions further include about 1% to about 20%, such as about 1% to about 15%, such as about 1% to about 10%, such as about 5% to about 15%, such as about 7% to about 12%, such as about 8% to about 11%, such as about 8.5% to about 11%, such as about 9.9% to about 10%, or such as about 9% by weight of a linear polymer, such as polyvinylpyrrolidone, e.g., PVP K-Series or Povidone K-30 marketed by AAA International Corp., Downers Grove, Ill., USA; PVP K-30 USP24 and industry grade, PVP VA-64, PVP K-17 and PVP K-90, marketed by Peakchem, Hangzhou, China.

Whitening Efficacy

In some embodiments, the dentifrice compositions have a whitening efficiency which is greater than a whitening efficiency of a comparative composition, which may include the same ingredients as a composition of the present disclosure, except that the comparative composition does not contain zinc. As used herein, the phrase "whitening efficacy" is intended to refer to the amount of change in tooth color. The color change can be measured according to the L*a*b* color scale. The luminance or lightness (L*) value measures brightness and varies from a value of one hundred for perfect white to zero for black, assuming a* and b* are zero. The a* value is a measure of redness when positive, gray when zero and greenness when negative. The b* value is a measure of yellowness when positive, gray when zero and blueness when negative. Generally, teeth appear whiter as: the L* value increases meaning they become brighter, the a* value increases or decreases, depending upon whether the stained teeth have a green tint or red tint prior to whitening, and the b* value decreases meaning they become less yellow. While this is the general relationship for perceived whitening, the b* value might also slightly increase if the magnitude of the increase of the L* value is large enough. Similarly, the L* value might also decrease if the magnitude of the decrease of the b* value is large enough to overshadow the less significant change in L*.

In some embodiments, the whitening index (W*) is used to assess tooth whiteness. The whiteness index is based on the distance of a color value from a nominal white point, represented in CIELAB colour space as L*=100, a*=0 and b*=0, and defined according to the following formula:

$$W^* = [(a^*)^2 + (b^*)^2 + (L^* - 100)^2]^{1/2}.$$

Changes in W* may be used to assess the whitening efficacy of a composition before and after a treatment. The following formula may be used to calculate ΔW*:

$$\Delta W^* = W^*(\text{Treatment}) - W^*(\text{baseline}).$$

Other values which may be used to assess tooth whiteness are described in Joiner et al., "A Review of Tooth Colour and Whiteness", *Journal of Dentistry*, 2008, 36S:S2-S7, herein incorporated by reference in its entirety.

Whitening efficacy of a composition may be determined by any method known in the art. For example, polished hydroxyapatite discs may be placed in sterile human saliva for 2 hours to allow a pellicle to form. The discs may then be rinsed in water and baseline color measurements made (using, for example, a Minolta chromameter CR300). The discs may then be brushed with (i) a composition of the present disclosure or (ii) a comparative composition. The brushing may be performed using a brushing machine. Following rinsing, the color of the discs may then be re-measured and the change in L*, a* and b* recorded for both treatment (i) and treatment (ii) and the W* and ΔW* values calculated. From a comparison of these data, any whitening efficiency of a composition is readily seen. Other methods for assessing whitening efficacy are described in the Examples, herein below.

Vehicle

In some embodiments, a whitening agent, complexed with a polymer or co-polymer, a (e.g., blue) pigment or dye, zinc, or a combination thereof, are combined with an orally acceptable vehicle to form a dentifrice. Such dentifrices may include a dental tablet, toothpaste (e.g., dental cream), tooth powders, a viscous liquid, such as a gel, a mouth wash, or any other form known to one of skill in the art. For example, the dentifrice may be a gel.

As used herein, an "orally acceptable vehicle" refers to a material or combination of materials that are safe for use in the stable whitening oral care dentifrice compositions of the present disclosure, commensurate with a reasonable benefit/risk ratio, with which the whitening agent, and other desired active ingredients may be associated while retaining significant efficacy. In some embodiments, the combination of ingredients is acidic to maintain stability of the whitening agent.

In some embodiments, the orally acceptable vehicle is a low water content orally acceptable vehicle and may include any known ingredients or additives. For example, the vehicle may include liquid mixtures of water, glycerin, and sorbitol. In some embodiments, the water content of the stable whitening dentifrice composition is less than about 3%, less than about 2%, less than about 1% or less than about 0.1% w/w. In other embodiments, the orally acceptable vehicle is a high water content orally acceptable vehicle and may include any known ingredients or additives. For example, the water content of the stable whitening dentifrice composition may be from about 3% to about 5% w/w, about 5% to about 10% w/w, about 10% to about 15% w/w, or about 15% to about 20% w/w.

In some embodiments, the orally acceptable vehicle is substantially anhydrous and includes a hydrophobic component, such as a polymer. The term "hydrophobic" or "water-insoluble" as applied to polymers and as employed herein refers to an organic polymer, which is substantially non-aqueous, and which has a water solubility of less than one gram per 100 grams of water at 25° C.

In some embodiments, the hydrophobic polymers suitable for use in the present orally acceptable vehicle are known in the art as "siloxane" polymers or "silicone" polymers. Some silicone-based hydrophobic polymers in accordance with the present disclosure include polyorganosiloxane polymers, such as polydimethylsiloxane.

In some embodiments, the siloxane polymers are in the form of a fluid. The polysiloxane fluids may include those with a viscosity at 25° C. of about 1 milliPascal-sec (mPa-s) to about 1000 mPa-s, or about 2 mPa-s to about 500 mPa-s or about 20 mPa-s to about 400 mPa-s. Suitable polysiloxane fluids may be linear or cyclic and may be substituted with a wide variety of substituents. In certain embodiments, the substituents include methyl, ethyl and phenyl substituents. Examples of linear polysiloxane and cyclic polymers in accordance with the present disclosure include dimethicone and cyclomethicone, respectively. Other suitable polysiloxane fluids include polysiloxane polyether copolymers and hydroxy-terminated polydimethyl-siloxane fluids, such as ST-DIMETHICONOL™ 40, SGM 36 and SGM3 from Dow Corning Corporation, Midland, Mich. Other suitable commercially available polysiloxane fluids include the DC200 series fluids marketed by Dow Corning Corporation and the AK Fluid series marketed by Wacker-Chemie GmbH, Munchen, Germany. High molecular silicone resins with a polysiloxane blend may also be used, including powdered trimethylsiloxysilicate, for example, which is commercially available from Dow Corning Corporation as 593 fluid or from Wacker Chemie AG, Munich, Germany as Wacker BELSIL® TMS 803. Another commercially available suitable silicone fluid is Q7-9210 from Dow Corning Corporation.

In other embodiments, the hydrophobic component may include a silicone pressure sensitive adhesive (PSA). PSAs can be produced by condensing a silicone resin and an organosiloxane, such as a polydiorganosiloxane. In some embodiments, the silicone polymers are prepared by mixing a silanol terminated polydiorganosiloxane, such as polydimethyl siloxane, with a silanol-containing silicone resin, whereby the silanol groups of the polydiorganosiloxane undergo a condensation reaction with the silanol groups of the silicone resin so that the polydiorganosiloxane is lightly crosslinked by the silicone resin. A catalyst, for example, an alkaline material, such as ammonia, ammonium hydroxide or ammonium carbonate, can be mixed with the silanol-terminated polydiorganosiloxane and the silicone resin to promote crosslinking. By copolymerizing the silicone resin with the silanol terminated polydiorganosiloxane, a polymer with self-adhering properties and a soft elastomer matrix can be produced.

Suitable PSA polymers in accordance with the present disclosure are described in U.S. Publication No. 2015/0037266 and U.S. Publication No 2005/0038181, which are each incorporated by reference herein in its entirety. Suitable commercially available PSA polymers include BIO-PSA polymers from the Dow Corning Corporation. These PSA polymers are available in three silicone resin to silicone polymer ratios, namely, 65/35 (low tack), 60/40 (medium tack), 55/45 (high tack). Without being bound by theory, it is believed that the variation in the ratio of silicone resin to polydiorganosiloxane results in the different tack properties of the BIO-PSA polymers.

In some embodiments, the hydrophobic component is present at a concentration from about 0% to about 80% by weight of the dentifrice composition of the present disclosure, such as about 40% to about 80% by weight, such as about 60% to about 80% by weight. In other embodiments, the hydrophobic component may be present in the dentifrice composition in an amount ranging from about 15% to about 25% by weight, such as about 16% to about 20% by weight, such as about 18% by weight.

In other embodiments, the present substantially anhydrous orally acceptable vehicle includes an ethylene oxide, propylene oxide block co-polymer, such as one having the formula (ethylene oxide)$_x$-(propylene oxide)$_y$, wherein x is an integer of 80-150, e.g., 100-130, e.g., about 118, and y is an integer of 30-80, e.g., about 60-70, e.g., about 66, having an average molecular weight of greater than 5000, e.g., 8000-13000 Da, e.g., about 9800. In some embodiments, the ethylene oxide, propylene oxide co-polymer is substantially free of an ethylene oxide, propylene oxide block co-polymer of average molecular weight less than 5000 Da. An example of a suitable commercially available ethylene oxide, propylene oxide co-polymer is PLURACARE® L1220 (available from BASF, Wyandotte, Mich., United States of America).

Other suitable low water content orally acceptable vehicles, which may be incorporated into the dentifrice composition of the present disclosure include, for example polyethylene glycol, such as PEG400, PEG600, PEG/PPG copolymers, such as PEG/PPG 38/8 copolymer, and PEG/PPG-1 16/66 copolymer sold as PLURACARE® L4370 and PLURACARE® L1220 from BASF, Wyandotte, Mich., respectively. In some embodiments, polyethylene glycol may be present in the dentifrice compositions in an amount ranging from about 0% to about 0.01%, about 0.01% to about 60%, or about 0% to about 15.0%, such as about 10%, about 6.3%, about 7.5%, or about 15% by weight.

In some embodiments, the low water content orally acceptable vehicles, which may be incorporated into the dentifrice composition of the present disclosure, include glycerin. In some embodiments, glycerin may be present in the dentifrice compositions in an amount ranging from about 0.01% to about 60%, such as about 35% by weight.

In some embodiments, the orally acceptable vehicle is present at a concentration from about 0% to about 80%, about 0.01% to about 60%, about 40% to about 80%, or about 60% to about 80%, by weight, of the dentifrice composition of the present disclosure. In other embodiments, the orally acceptable vehicle is present in the dentifrice composition of the present disclosure in an amount ranging from about 15% to about 35%, or about 16% to about 20%, by weight. In another example, the orally acceptable vehicle is present in the dentifrice composition of the present disclosure in an amount ranging from about 6% to about 7.5% by weight.

In some embodiments, the orally acceptable vehicle further includes a polymer, which aids in the deposition of a pigment, such as blue pigment ("pigment deposition aid"). Without wishing to be bound by theory, it is believed that a pigment deposition aid works by having affinity for both the pigment and the surface of the teeth, the deposition aid serving as a link between the two.

Pigment deposition aids for use in accordance with the present disclosure may be or include high molecular weight polymers, i.e. polymers having a molecular weight of 200,000 or greater. Suitable pigment deposition aids include hydroxypropylmethylcellulose polymers, for example, hydroxypropylmethylcellulose polymers having a viscosity (mPa-s) at 20° C. of about 3.200 to about 4.800 using capillary viscometry. Suitable commercially available hydroxypropylmethylcellulose polymers include WALOCEL® HM 4000PA-2910 from Covestro AG, Leverkusen, Germany. Other suitable pigment deposition aids include those described in European Patent No. 1935395, such as GANTREZ™ polymers, which is herein incorporated by reference in its entirety.

The pigment deposition aid is incorporated into the instant stable whitening oral care dentifrice compositions in an amount from about 0%, about 0.01% to about 10%, about 0.05% to about 5%, or about 0.1% to about 1%, by weight.

In one embodiment, the pigment deposition aid is able to enhance the whitening efficacy of the dentifrice composition in comparison to a dentifrice composition that does contain a pigment deposition aid, by at least 5% and more typically by at least 25%.

In some embodiments, the viscosity of the instant stable whitening oral care dentifrice compositions is from about 1,000 centipoise (cPs) to about 900,000 cPs, such as about 10,000 cPs to about 100,000 cPs, such as about 50,000 cPs to about 900,000 cPs, such as about 200,000 cPs to about 600,000 cPs.

In some embodiments, the orally acceptable vehicle may further include surfactants. In some embodiments, the surfactants enhance stability of the formulation, help clean the oral cavity surfaces through detergency, and provide foam upon agitation, e.g., during brushing with a dentifrice composition of the disclosure. Surface active agents generally achieve increased whitening action, by thoroughly dispersing the whitening agent throughout the oral cavity. In various embodiments, suitable surface active agents may function as a surface active agent, emulsifier, and/or foam modulator.

Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium cocoyl monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

In some embodiments, one or more surfactants may be present in a total amount of from about 0.1% to about 4% w/w. In some embodiments, one or more surfactants may be present in a total amount from about 1.0% to about 2.5% w/w. In some embodiments, one or more surfactants may be present in a total amount of about 1 to about 2% w/w. In some embodiments, one or more surfactants may be present in a total amount of about 1.5% w/w.

In some embodiments, the dentifrice composition of the present disclosure, optionally, includes a thickening agent. Any orally acceptable thickening agent can be used, including without limitation carbomers, also known as carboxyvinyl polymers, carrageenans, also known as Irish moss and more particularly carrageenan (iota-carrageenan), high molecular weight polyethylene glycols (such as CARBOWAX™, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. In some embodiments, the one or more optional thickening agents are present in a total amount of about 0.1% to about 90% w/w. In some embodiments, the one or more optional thickening agents are present in a total amount of about 1% to about 50% w/w, such as about 1.75%. In some embodiments, the one or more optional thickening agents are present in a total amount of about 5% to about 35% w/w.

In some embodiments, the present compositions optionally include an antioxidant. Acceptable antioxidants include BHA, BHT, vitamin A, carotenoids, vitamin E, flavonoids, polyphenols, ascorbic acid, herbal antioxidants, chlorophyll, melatonin and mixtures thereof. In some embodiments, the one or more antioxidants are optionally present in a total amount of about 0.01% to about 0.1% w/w, such as about 0.03%, by weight.

Useful flavoring agents include any material or mixture of materials operable to enhance the taste of the composition. Any orally acceptable natural or synthetic flavoring agent can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and mixtures thereof.

In some embodiments, one or more flavoring agents are optionally present in a total amount of about 0.01% to about 5% w/w, about 0.05% to about 2% w/w, about 0.1% to about 2.5% w/w, about 0.1% to about 0.5% w/w, or about 1.4% w/w.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some embodiments optionally include one or more sweeteners. In some embodiments, the one or more optional sweeteners are present in a total amount from about 0.005% to about 5% w/w or about 0.01 to about 1% w/w.

pH modifying agents among those useful herein include acidifying agents to lower pH, basifying agents to raise pH and buffering agents to control pH within a desired range. For example, one or more compounds selected from acidifying, basifying and buffering agents can be included to provide a pH of 2 to 10, or in various embodiments from 2 to 8, from 3 to 9, from 4 to 8, from 5 to 7, from 6 to 10, and from 7 to 9. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range.

Colorants, mouth-feel agents and/or others additives may also be included, if desired, in the present compositions.

Other Active Ingredients

The dentifrice compositions of the present disclosure optionally include one or more further active material(s), which is operable for the prevention or treatment of a condition or disorder of hard or soft tissue of the oral cavity, the prevention or treatment of a physiological disorder or condition, or to provide a cosmetic benefit.

Some embodiments of the present disclosure include a dental abrasive or combination of dental abrasive agents. As used herein, the term "abrasive" or "abrasive agent" also includes materials commonly referred to as "polishing agents." Any orally acceptable abrasive can be used, but typically, type, fineness (particle size) and amount of abrasive should be selected so that tooth enamel is not excessively abraded in normal use of the composition. Suitable abrasives include without limitation silica (in the form of silica gel, hydrated silica or precipitated silica), alumina, insoluble phosphates, calcium carbonate, resinous abrasives such as urea-formaldehyde condensation products and the like.

Among insoluble phosphates useful as abrasives are orthophosphates, polymetaphosphates and pyrophosphates. Illustrative examples are dicalcium orthophosphate dihydrate, calcium pyrophosphate, n-calcium pyrophosphate, tricalcium phosphate, calcium polymetaphosphate and insoluble sodium polymetaphosphate.

Average particle size of an abrasive, if present, is generally about 0.1 to about 30 μm for example about 1 to about 20 μm or about 5 to about 15 μm. In some embodiments, one or more abrasives are present in an amount of about 0.01% to about 40% w/w, such as 0.01% to about 10%, such as 1.75%. In some embodiments, the abrasive is calcium pyrophosphate. In some embodiments, the calcium pyrophosphate is present in an amount from about 5% to about 50% w/w, such as about 20%.

In various embodiments of the present disclosure, the dentifrice composition includes an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent is present in an amount of about 0.1% to about 30% w/w. In some embodiments, the dentifrice composition includes a mixture of anticalculus agents. In some embodiments, tetrasodium pyrophosphate (TSPP) and sodium tripolyphosphate (STPP) are used as the anticalculus agents. In some embodiments, the anticalculus agent includes about 0.01% to about 5% w/w TSPP, such as about 2%.

Another component of the present compositions may be a synthetic anionic polymeric polycarboxylate (SAPP), which acts as a stabilizer for the polyphosphate anti-tartar agent and which may help to block access of painful or pain-causing materials, such as sugars, to the tooth nerves.

In some embodiments, the dentifrice composition optionally includes a source of fluoride ions. In some embodiments, the source of fluoride ions is selected from: fluoride, monofluorophosphate (MFP), and fluorosilicate salts. In some embodiments, one or more fluoride ion-releasing compounds are optionally present in an amount providing a total of 100 to 20,000 ppm, 200 to 5,000 ppm, or 500 to 2,500 ppm, fluoride ions. If present, the amount of fluoride in the present composition ranges from about 0.1% to 1.1%, typically about 1.1%.

The compositions also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The compositions of the present disclosure may optionally include an antimicrobial (e.g., antibacterial) agent in addition to the zinc salts described herein. An illustrative list of useful antibacterial agents is provided in U.S. Pat. No. 5,776,435 to Gaffar et al., the contents of which are incorporated herein by reference. One or more antimicrobial agents in addition to the zinc salts described herein are optionally present in an antimicrobial effective total amount, typically about 0.05% to about 10%, for example about 0.1% to about 3%.

Methods

In various embodiments, the present disclosure provides methods to whiten an oral surface in a human or animal subject. The method may include contacting a tooth surface with the dentifrice composition of the present disclosure. As used herein "animal subject" includes non-human mammals such as canines, felines and horses. The stable whitening dentifrice composition is contacted with an oral surface of the mammalian subject to thereby whiten teeth in a highly efficacious manner.

In various embodiments, the dentifrice composition prepared in accordance with the present disclosure may be applied regularly to an oral surface, for example on a daily basis, at least one time daily for multiple days, or alternately every second or third day. In some embodiments, the dentifrice composition is applied to the oral surfaces from 1 to 3 times daily, for at least 2 weeks up to 8 weeks, from four months to three years, or more up to a lifetime.

In some embodiments, the dentifrice composition, such as a gel, may be applied directly to the teeth using a delivery device, such as a pen, e.g., a COLGATE® whitening pen or a COLGATE® ACTIS™ whitening pen, Colgate-Palmolive Company, New York, N.Y., a liquid stick having an applicator, such as a felt tip, brush, roller ball, or non-woven pad, sufficient to effect whitening. In some embodiments, the stable whitening dentifrice composition of the present disclosure is maintained on the surface of the tooth for a plurality of minutes.

In some embodiments, the composition is maintained on the surface of a tooth for from about 1 minute to about 8 hours. In some embodiments, the composition is maintained on the surface of a tooth for from about 5 minutes to about 4 hours. In some embodiments, the composition is maintained on the surface of a tooth for from about 10 minutes to about 120 minutes. In some embodiments, the composition is maintained on the surface of a tooth for from about 15 minutes to about 60 minutes. In some embodiments, the composition is maintained on the surface of a tooth for from about 20 minutes to about 45 minutes.

Some embodiments provide a method where a delivery device, such as a whitening pen is stored within an oral care implement, such as a toothbrush. In some embodiments, the delivery device, such as a whitening pen is removed from the oral care implement prior to application of the composition to the tooth. In some embodiments, the composition is applied to the tooth after brushing with the oral care implement.

The examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

EXAMPLES

Example 1

$\Delta W$ During Brushing Studies

In Example 1, brushing occurred for two minutes, and then the $\Delta W$ was measured at the conclusion of the brushing and then at 10 minute intervals thereafter. The efficacy of zinc was tested in six (6) simple solutions, as shown in Tables 1 and 2. In Table 1, the first simple solution is a reference solution which includes 0.05% blue pigment 15 CI 74160 in glycerin. The reference solution does not include zinc. The other five (5), non-reference solutions include: 0.05% blue pigment 15 CI 74160 in glycerin with 2% zinc lactate, 0.05% blue pigment 15 CI 74160 in glycerin with 2% zinc citrate, 0.05% blue pigment 15 CI 74160 in glycerin with 2% zinc chloride, 0.05% blue pigment 15 CI 74160 in glycerin with 2% zinc oxide, and 0.05% blue pigment 15 CI 74160 in glycerin with 2% zinc phosphate. Table 2 includes the same six (6) simple solutions, except that the 0.05% blue pigment is replaced with 0.05% blue dye No. 1 42090.

Each solution was used to brush a set of 12 human teeth and conduct a 30 minute measurement cycle (e.g., to test retention). Thus, each solution was applied to the human teeth by brushing. The $\Delta W$ was calculated for each solution at 10 minute time intervals, and the non-reference solutions were compared against the reference solution.

Of the solutions including zinc salts, the initial $\Delta W$ was found to be greatest in the presence of 2% zinc lactate despite the fact that zinc lactate includes fewer zinc ions than zinc chloride, zinc oxide, zinc citrate, and zinc phosphate. Of the solutions including the blue pigment (Table 1), the solutions including the zinc salts provided greater initial whitening benefits (e.g., a greater $\Delta W$ at time=0) than the solution without a zinc salt. Of the solutions including the blue dye (Table 2), the solutions including the zinc salts, particularly zinc lactate, provided greater initial whitening benefits (e.g., a greater $\Delta W$ at time=0, with the exception of the zinc chloride solution) and longer lasting whitening benefits (e.g., a greater $\Delta W$ at time=10 min, 20 min, 30 min) than the solution without a zinc salt solution.

TABLE 1

ΔW Results for simple solution (i.e., glycerin) with blue pigment with and without zinc
0.05% blue pigment in glycerin

|  | Without Zinc ΔW | Zinc Lactate 2% ΔW | Zinc Chloride 2% ΔW | Zinc Oxide 2% ΔW | Zinc Citrate 2% ΔW | Zinc Phosphate 2% ΔW |
| --- | --- | --- | --- | --- | --- | --- |
| Initial | 2.57 | 5.70 | 3.50 | 3.51 | 3.18 | 2.99 |
| 10 min | 2.22 | 2.08 | 2.67 | 2.26 | 1.56 | 1.80 |
| 20 min | 1.71 | 1.79 | 2.17 | 1.67 | 1.63 | 1.84 |
| 30 min | 1.82 | 1.80 | 1.93 | 1.39 | 1.10 | 2.10 |

TABLE 2

ΔW Results for simple solution (i.e., glycerin) with blue dye with and without zinc
0.05% blue dye in glycerin

|  | Without Zinc ΔW | Zinc Lactate 2% ΔW | Zinc Chloride 2% ΔW | Zinc Oxide 2% ΔW | Zinc Citrate 2% ΔW | Zinc Phosphate 2% ΔW |
| --- | --- | --- | --- | --- | --- | --- |
| Initial | 7.63 | 11.47 | 7.44 | 8.98 | 8.91 | 8.71 |
| 10 min | 1.66 | 6.67 | 4.70 | 5.25 | 3.73 | 4.90 |
| 20 min | 1.51 | 4.23 | 3.35 | 3.68 | 1.70 | 3.07 |
| 30 min | 0.24 | 3.45 | 2.30 | 3.33 | 1.18 | 2.28 |

The efficacy of the zinc lactate was then tested in high water and low water toothpaste matrices, as shown in Table 3. In Table 3, the toothpaste matrices include (1) a reference toothpaste matrix that includes blue pigment and no zinc, (2) a reference toothpaste matrix that includes blue dye and no zinc, (3) a toothpaste matrix that includes low water, blue dye, and 2% zinc lactate, and (4) a toothpaste matrix that includes high water, blue dye, and 2% zinc lactate. The compositions of the four toothpaste respective matrices are shown in Table 4.

Each toothpaste matrix in Tables 3 and 4 was used to brush a set of 12 human teeth and conduct a 30 minute measurement cycle (e.g., to test retention). The ΔW was calculated for each toothpaste matrix at 10 minute time intervals and the non-reference toothpaste matrices were compared against the reference toothpaste matrices.

The low water toothpaste matrix with the blue dye and 2% zinc lactate (Option 1) provided greater initial whitening benefits (e.g., a greater ΔW at time=0) and longer lasting whitening benefits (e.g., a greater ΔW at time=10 min, 20 min, 30 min) than the low water reference toothpaste with blue dye and no zinc (Reference blue dye). In addition, the high water toothpaste matrix with blue dye and 2% zinc lactate (Option 2) provided whitening benefits that were as good or better than the low water toothpaste matrix with blue dye and no zinc (Reference blue dye) both initially (e.g., at time=0) and over time (e.g., at time=10 min, 20 min, 30 min).

TABLE 3

ΔW Results for Toothpaste Matrices

|  | Reference blue pigment Commercial formula containing blue pigment ΔW | Reference blue dye (low water) Commercial formula containing blue dye ΔW | Option 1 (low water) Experimental formula containing blue dye and 2% Zn Lactate, with low water ΔW | Option 2 (high water) Experimental formula containing blue dye and 2% Zn Lactate, with high water ΔW |
| --- | --- | --- | --- | --- |
| Initial | 9 | 13 | 15 | 13 |
| 10 min | 8 | 7 | 11 | 8 |
| 20 min | 7 | 5 | 8 | 6 |
| 30 min | 7 | 4 | 6 | 4 |

TABLE 4

Compositions of Toothpaste Matrices in Table 3

|  | Reference Blue Pigment | Reference Blue Dye (low water) | Option 1 (low water) | Option 2 (high water) |
| --- | --- | --- | --- | --- |
| Water | 29.16 | 15 | 15 | 27.42 |
| Humectant | 33.44 | 49.88 | 49.88 | 33.44 |
| Silica | 26 | 27 | 27 | 26 |
| Sodium Fluoride | 0.32 | 0.22 | 0.22 | 0.32 |
| Sweetener | 0.3 | 0.5 | 0.5 | 0.3 |
| Gum | 0.7 | 0.55 | 0.55 | 0.7 |
| Polymer |  | 1 | 1 |  |
| Polyphosphates | 5.44 |  |  | 5.44 |
| Surfactant | 2.75 | 1.5 | 1.5 | 2.75 |
| Base | 0.14 |  |  | 0.14 |
| Zinc |  | 2 | 2 | 2 |
| Flavor | 1.2 | 1.3 | 1.3 | 1.2 |
| Blue dye |  | 0.05 | 0.05 | 0.05 |

TABLE 4-continued

Compositions of Toothpaste Matrices in Table 3

|  | Reference Blue Pigment | Reference Blue Dye (low water) | Option 1 (low water) | Option 2 (high water) |
| --- | --- | --- | --- | --- |
| Mica | 0.25 | 1 | 1 | 0.25 |
| Pigment film | 0.3 |  |  |  |
| red coloring agent | 0.0003 |  |  |  |
| blue coloring agent | 0.0002 |  |  |  |

What is claimed is:

1. A whitening dentifrice composition comprising:
a blue coloring agent, wherein the blue coloring agent is a blue dye present in 0.05% weight;
a zinc salt, wherein the zinc salt is selected from the group consisting of zinc lactate, zinc oxide, zinc chloride, zinc phosphate, and zinc citrate, wherein the zinc salt is present in an amount from about 0.5 wt % to about 2.5 wt %;
wherein the whitening dentifrice composition provides a greater whitening benefit to a tooth surface in comparison to a dentifrice composition that does not contain the zinc salt;
an orally acceptable vehicle;
wherein the orally acceptable vehicle includes glycerin and is a low water content wherein the amount of water is from about 0% to about 25%;
a dental abrasive agent, comprising silica gel, hydrated silica, precipitated silica, alumina, insoluble phosphates, calcium carbonate, resinous abrasives; wherein the dental abrasive is from 0.01% to 40%; and
wherein the whitening dentifrice composition does not include hydrogen peroxide and core shell silica.

2. The whitening dentifrice composition of claim 1, wherein the zinc salt is present in an amount of about 2.00 wt %.

3. The whitening dentifrice composition of claim 2, wherein the zinc salt comprises zinc lactate, and wherein the whitening dentifrice composition including the zinc lactate provides a greater initial whitening benefit and a longer-lasting whitening benefit to the tooth surface than a dentifrice composition including other zinc salts or no zinc salt.

4. The whitening dentifrice composition of claim 3, wherein the whitening dentifrice composition further comprises water in an amount of about 15.00%.

5. A whitening dentifrice composition comprising:
a blue dye present in 0.05% weight;
a zinc salt present in an amount of about 2.00 wt %;
wherein the zinc salt is selected from the group consisting of zinc lactate, zinc oxide, zinc chloride, zinc phosphate, and zinc citrate;
water in an amount from about 0.00% to about 25.00%, wherein the whitening dentifrice composition including the zinc salt provides a greater initial whitening benefit and a longer-lasting whitening benefit to a tooth surface than a dentifrice composition including the same amount of water and no zinc salt;
an orally acceptable vehicle;
a dental abrasive agent comprising silica gel, hydrated silica, precipitated silica, alumina, insoluble phosphates, calcium carbonate, resinous abrasives; wherein the dental abrasive is from 0.01% to 40%; and
wherein the whitening dentifrice composition does not include a peroxide compound and does not include hydrogen peroxide and core shell silica.

6. The whitening dentifrice composition of claim 5, wherein the zinc salt comprises zinc lactate.

7. The whitening dentifrice composition of claim 5, wherein the whitening dentifrice composition including the zinc salt provides a substantially equal initial whitening benefit to the tooth surface in comparison to a dentifrice composition including from about 3 wt % to about 4 wt % less water and no zinc salt.

8. The whitening dentifrice composition of claim 5, wherein, 30 minutes after application, the whitening dentifrice composition including the zinc salt provides a whitening benefit to the tooth surface that is equal to a dentifrice composition including from about 3 wt % to about 4 wt % less water and no zinc salt.

9. The whitening dentifrice composition of claim 5, wherein the dental abrasive agent is present in an amount of about 15%.

10. A method for whitening a tooth surface in a human or animal, the method comprising:
applying a whitening dentifrice composition to the tooth surface, wherein the whitening dentifrice composition comprises:
a blue coloring agent, wherein the blue coloring agent is a dye present in 0.05% weight;
zinc lactate present in an amount of about 2.00 wt %, wherein the whitening dentifrice composition provides a greater whitening benefit to the tooth surface than a dentifrice composition including other zinc salts or no zinc salt;
a dental abrasive agent present in an amount of about 15%;
a low water content is from about 0.00% to about 25.00%; and
an orally acceptable vehicle; and
wherein the whitening dentifrice composition does not include hydrogen peroxide and core shell silica.

* * * * *